(12) United States Patent
Kuroda et al.

(10) Patent No.: US 8,893,544 B2
(45) Date of Patent: Nov. 25, 2014

(54) VISCOSITY MEASURING DEVICE AND VISCOSITY MEASURING METHOD

(75) Inventors: Masaharu Kuroda, Tsukuba (JP);
Hiroshi Yabuno, Yokohama (JP)

(73) Assignee: National Institute of Advanced Industrial Science and Technology, Chiyoda-ku, Tokyo (JP)

( * ) Notice: Subject to any disclaimer, the term of this patent is extended or adjusted under 35 U.S.C. 154(b) by 378 days.

(21) Appl. No.: 13/522,866

(22) PCT Filed: Jan. 7, 2011

(86) PCT No.: PCT/JP2011/000039
§ 371 (c)(1),
(2), (4) Date: Jul. 18, 2012

(87) PCT Pub. No.: WO2011/086879
PCT Pub. Date: Jul. 21, 2011

(65) Prior Publication Data
US 2012/0291528 A1 Nov. 22, 2012

(30) Foreign Application Priority Data

Jan. 18, 2010 (JP) ................................. 2010-008402

(51) Int. Cl.
*G01N 11/16* (2006.01)
(52) U.S. Cl.
CPC ...................................... *G01N 11/16* (2013.01)
USPC ........................................ 73/54.41; 73/54.01
(58) Field of Classification Search
USPC .................... 73/54.01, 54.41, 64.53
See application file for complete search history.

(56) References Cited

U.S. PATENT DOCUMENTS

| | | | | |
|---|---|---|---|---|
| 5,766,137 | A * | 6/1998 | Omata .......................... | 600/587 |
| 5,777,232 | A * | 7/1998 | Kurita et al. .................... | 73/664 |
| 7,570,061 | B2 * | 8/2009 | Kuroda et al. ................. | 324/327 |
| 2007/0294042 | A1 * | 12/2007 | Kuroda et al. .................. | 702/56 |
| 2009/0064771 | A1 * | 3/2009 | Dick et al. ....................... | 73/105 |
| 2009/0293161 | A1 * | 11/2009 | Kuroda et al. .................. | 850/33 |

FOREIGN PATENT DOCUMENTS

| | | |
|---|---|---|
| JP | 08-267008 | 10/1996 |
| JP | 09-145691 | 6/1997 |
| JP | 2004-361300 | 12/2004 |
| JP | 2007-093573 | 4/2007 |
| JP | 2010-002409 | 1/2010 |

OTHER PUBLICATIONS

Kato et al., "Nonlinear Dynamics of Microcantilever Probe", Dynamics and Design Conference (CD-ROM) 2009, Ronbun No. 247.
Azuma et al., "Nonlinear Dynamics of Self-Excited Cantilever", Dynamics and Design Conference (CD-ROM), 2009, Ronbun No. 487.

(Continued)

*Primary Examiner* — Hezron E Williams
*Assistant Examiner* — Hoang Nguyen
(74) *Attorney, Agent, or Firm* — Young Basile Hanlon & MacFarlane P.C.

(57) ABSTRACT

The oscillating velocity of an oscillating body in a fluid to be measured is positively fed back, so as to activate an actuator. The oscillating state of the oscillating body is monitored while making a velocity feedback gain increase. The velocity feedback gain when the oscillating body has oscillated is obtained as an oscillation limit gain at the oscillation limit, and this oscillation limit gain is used as a viscosity equivalent value representing viscosity of the measured fluid.

9 Claims, 8 Drawing Sheets

(56) References Cited

OTHER PUBLICATIONS

Hayashi et al., "Amplitude Control in van der Pol Type Self-excited Micro Cantilever for AFM", Transactions of the Japan Society of Mechanical Engineers, Series C, Aug. 25, 2007, vol. 73, No. 732, pp. 2225-2231.

English translation of International Preliminary Report on Patentability in PCT/JP2011/000039, mailed Aug. 16, 2012.

* cited by examiner

VISCOSITY MEASURING DEVICE AND VISCOSITY MEASURING METHOD

TECHNICAL FIELD

The present invention relates to a viscosity measuring method and a viscosity measuring device using an oscillating body.

BACKGROUND

Viscometers for measuring viscosity of a fluid are generally classified according to basic principles into a capillary viscometer, a falling sphere viscometer, a rotational viscometer, a chemical viscometer, and an oscillating viscometer.

Of these types of viscometers, in JP 2004-361300 A, for example, there is proposed a oscillating viscometer for calculating viscosity of a measured object based on a driving current generated due to an inductor plate being electromagnetically oscillating with a predetermined amplitude, or there is proposed a oscillating viscometer for calculating viscosity of the same by making an oscillating body externally excite, obtaining a frequency response curve representing relationship between excitation frequency and corresponding response amplitude of the oscillating body, and finding a Q value thereof.

SUMMARY

As mentioned above, the method for calculating viscosity based on the Q value, which is acquired from the frequency response curve, requires a frequency response curve calculated experimentally beforehand. To attain such a curve, it is necessary to sweep excitation frequency in a broad frequency range, and find a response amplitude of the oscillating body in each frequency, which is troublesome.

In addition, since the frequency response curve obtained experimentally cannot provide a clear resonance peak as is shown in FIG. 4A when the oscillating body is in a liquid, it is difficult to correctly read a resonance point from the frequency response curve and find a precise Q value. Therefore, there is a problem that improving accuracy of viscosity measurement is difficult.

The present invention has been made in light of the above-mentioned unsolved problem, and has an object to provide a viscosity measuring method and a viscosity measuring device, which can easily measure viscosity with high precision.

In order to achieve the above object, according to an aspect of the present invention, there is provided a viscosity measuring method, using a viscosity measuring device comprising: an oscillating body put in a fluid to be measured; an actuator for making the oscillating body oscillate self-excitedly; an oscillating velocity detector for detecting oscillating velocity of the oscillating body; and a controller of positive feedback of the oscillating velocity detected by the oscillating velocity detector, to activate the actuator according to a feedback control signal Fs represented by an equation: $Fs=Cc \cdot (dx/dt)$, where Fs denotes a feedback control signal, Cc denotes a positive linear velocity feedback gain, and dx/dt denotes oscillating velocity of the oscillating body; wherein the viscosity measuring method comprises the steps of: changing the linear velocity feedback gain for the feedback control; and using as an oscillation limit gain for giving an oscillation limit the linear velocity feedback gain at the time when the oscillating body changes between a non-oscillation mode and an oscillating mode, and detecting the oscillation limit gain as a viscosity equivalent value representing viscosity of the fluid.

In addition, in the above method, the viscosity measuring device may further comprise a oscillating displacement detector for detection of oscillating displacement of the oscillating body, and the controller comprises a response amplitude reducer for reduction of response amplitude of the oscillating body based on the oscillating velocity and the oscillating displacement detected by the oscillating displacement detector; feedback control is carried out in order to activate the actuator according to a feedback control signal Fs represented by an equation: $Fs=(Cc-Cnon \cdot x^2) \cdot (dx/dt)$, where Fs denotes a feedback control signal, Cc denotes a positive linear velocity feedback gain, Cnon denotes a positive non-linear feedback gain, x denotes oscillating displacement of the oscillating body, and dx/dt denotes oscillating velocity of the oscillating body.

Furthermore, the above method may further comprise a step of calculating viscosity $\eta$ of the fluid using an equation: $\eta=\{2/(\rho \cdot \omega)\} \times (Cc/S)^2$, where $\rho$ denotes density of the fluid to be measured, $\omega$ denotes a response frequency of the oscillating body, Cc denotes the linear velocity feedback gain, S denotes area of the oscillating body facing the fluid; wherein the oscillation limit gain is used as the linear velocity feedback gain Cc, and the response frequency of the oscillating body is used as the response frequency $\omega$ when the linear velocity feedback gain is the oscillation limit gain. When the linear feedback gain Cc is increased, the gain at which the self-excited oscillation starts in the oscillating body can be found. This value is called the oscillation limit gain Cc*, which is equivalent to the viscosity of the fluid.

Moreover, in the above method, the oscillating body may be a cantilever.

Additionally, according to another aspect of the present invention, there is provided a viscosity measuring device, comprising: an oscillating body put in a fluid to be measured; an actuator for making the oscillating body oscillate self-excitedly; an oscillating velocity detector for detection of oscillating velocity of the oscillating body; a controller of positive feedback of the oscillating velocity detected by the oscillating velocity detector, so as to activate the actuator according to a feedback control signal Fs represented by an equation: $Fs=Cc \cdot (dx/dt)$, where Fs denotes a feedback control signal, Cc denotes a positive linear velocity feedback gain, and dx/dt denotes oscillating velocity of the oscillating body; a gain adjustor for changing the linear velocity feedback gain of the feedback controller; and a viscosity equivalent value detector for setting the linear velocity feedback gain at the time when the oscillating body changes between a non-oscillation mode and an oscillating mode as an oscillation limit gain for giving an oscillation limit, and detecting the oscillation limit gain as a viscosity equivalent value representing viscosity of the fluid.

According to the present invention, an oscillating body in fluid to be measured is oscillating self-excitedly through feedback control using an actuator where positive feedback of an oscillating velocity is performed. Therefore, when a linear velocity feedback gain is changed, and once it reaches the oscillation limit, the oscillating body will start self-excited oscillation for the first time. The oscillation limit gain, which is the linear velocity feedback gain at the oscillation limit, represents a viscosity equivalent value. Therefore, whether the oscillating body is oscillating will be determined clearly, and the linear velocity feedback gain at that time, namely the oscillation limit gain, will be obtained as a viscosity equivalent value. Use of this viscosity equivalent value allows easy detection of viscosity of the measured fluid with high precision.

In particular, a response amplitude reducer is provided, performing feedback of linear components based on oscillating velocity and nonlinear components based on oscillating displacement and the oscillating velocity. This allows adjustment of the nonlinear components, thereby allowing adjustment of the response amplitude of the oscillating body. Adjustment of the response amplitude of the oscillating body prevents generation of an eddy in the measured fluid, and keeps laminar flow. That is, accuracy of viscosity measurement may be improved.

Furthermore, calculation of viscosity η of the liquid to be measured using the response frequency of the oscillating body at the time when the linear velocity feedback gain Cc is the oscillation limit gain, namely using the response frequency equivalent to the natural frequency of the oscillating body, allows improvement in conversion precision of viscosity η using an equation: "$\eta=\{2/(\rho\cdot\omega)\}\times(Cc/S)^2$", and provision of highly precise viscosity.

In particular, reduction in the response amplitude will make the response frequency of the oscillating body take a value near the linear natural frequency of the oscillating body even if the linear velocity feedback gain is a little larger than the oscillation limit gain. Therefore, with the reduced response amplitude, calculation of the viscosity using the response frequency of the oscillating body when the linear velocity feedback gain is near the oscillation limit gain as response frequency ω in the equation will find viscosity with high precise.

DETAILED DESCRIPTION

Embodiments of the present invention will now be described below. First, the first embodiment will be described.

Figure 1:
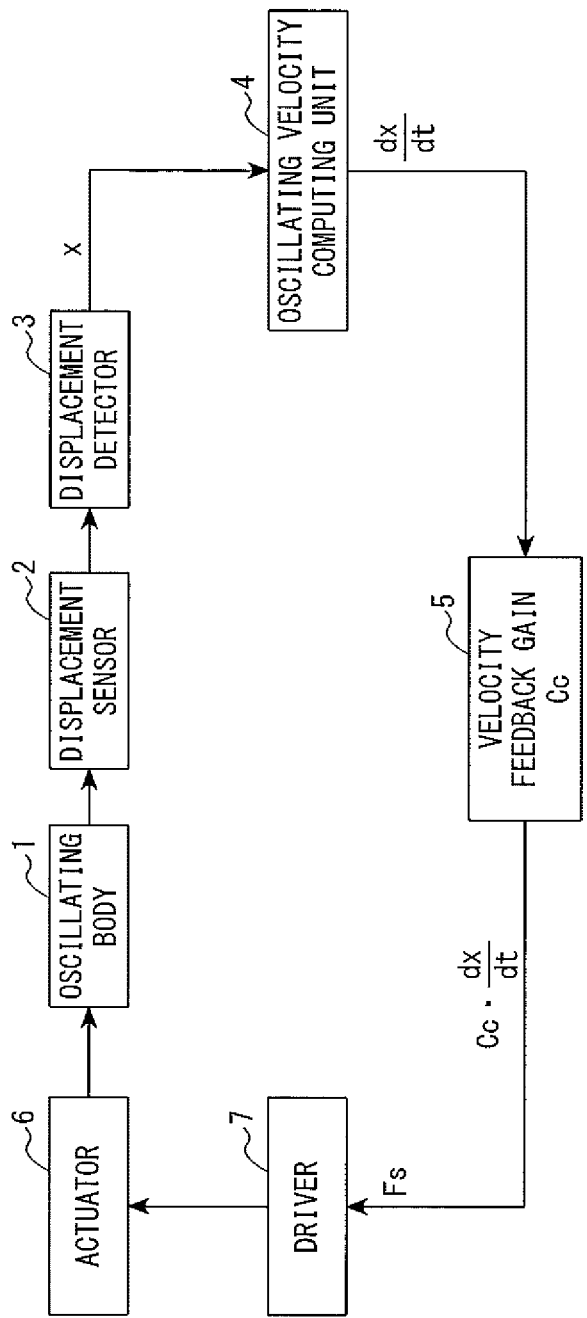
FIG. 1 is a schematic block diagram showing a working example of a viscosity measuring device, according to a first embodiment of the present invention.

FIG. 1 is a schematic block diagram showing a working example of a viscosity measuring device, according to the present invention. In FIG. 1, reference numeral 1 denotes an oscillating body, such as cantilever; 2 denotes a displacement sensor for measurement of oscillating displacement of the oscillating body; 3 denotes a displacement detector; 4 denotes an oscillating velocity computing unit; 5 denotes an amplifier; 6 denotes an actuator for oscillating the oscillating body 1; and 7 denotes a driver for driving the actuator 6.

The displacement sensor 2 is, for example, constituted by a piezo-electric element. Output of the displacement sensor 2 enters the displacement detector 3, and the displacement detector 3 then detects a displacement of the oscillating body 1. For example, when the cantilever is used as the oscillating body 1, the displacement detector 3 may be constituted by a signal conditioner, such as a charge amplifier. The deflection of the cantilever, which is detected by the displacement detector 3, is equivalent to an oscillating displacement x of the cantilever.

The displacement detector 3 transmits the detected oscillating displacement x of the detected oscillating body 1 to the oscillating velocity computing unit 4.

The oscillating velocity computing unit 4 is constituted by a differentiator, receives the oscillating displacement x from the displacement detector 3, differentiates the received oscillating displacement x to find the oscillating velocity of the oscillating body 1 or dx/dt, and then transmits the calculated dx/dt to the amplifier 5.

The amplifier 5 is constituted by a variable amplifier, receives the oscillating velocity dx/dt from the oscillating velocity computing unit 4, multiplies the received oscillating velocity dx/dt by a velocity feedback gain Cc, which is a positive linear feedback gain, calculates Cc×dx/dt, and outputs to the driver 7 the calculated value of Cc×dx/dt as a feedback control signal Fs.

The actuator 6 is constituted by a piezo-electric element, for example, and configured for the oscillating body 1 to make a self-excited oscillation by the actuator 6 driving the oscillating body 1.

The driver 7 is constituted by, for example, an amplifier for driving the piezo-electric element, amplifies the feedback control signal Fs received from the amplifier 5, and outputs it to the actuator 6, thereby driving the actuator 6.

A viscosity measuring method according to the first embodiment will be explained below.

To begin with, the oscillating body 1 is put in a fluid to be measured for viscosity. The driver 7 is activated, making a positive feedback of the oscillating velocity dx/dt. At this time, a predetermined initial value, such as a comparatively small value, is set to the velocity feedback gain Cc.

With such a configuration, the driver 7 drives the actuator 6, which then applies force or momentum to the oscillating body 1. Displacement of the oscillating body 1 is detected by the displacement sensor 2, and the displacement detector 3 then detects an oscillating displacement x of the oscillating body 1 based on the output of the displacement sensor 2. This oscillating displacement x is transmitted to the oscillating velocity computing unit 4, which then calculates oscillating velocity dx/dt.

The amplifier 5 multiplies the oscillating velocity dx/dt by the velocity feedback gain Cc, and transmits the calculated value of Cc×dx/dt to the driver 7 as the feedback control signal Fs. The driver 7 amplifies the feedback control signal Fs, driving the actuator 6. The actuator 6 then applies force or momentum to the oscillating body 1.

With the actuator 6 being controlled in such a manner, whether the oscillating body 1 has oscillated is monitored based on, for example, the oscillating displacement x, which is calculated by the displacement detector 3, or the oscillating velocity dx/dt, which is calculated by the oscillating velocity computing unit 4. When the velocity feedback gain Cc is comparatively small, the oscillating body 1 does not oscillate.

When the oscillating body 1 does not oscillate, the velocity feedback gain Cc is made to increase, thereby increasing the feedback control signal Fs, and increasing force or momentum applied to the oscillating body 1 by the actuator 6. When the oscillating body 1 starts oscillation, the velocity feedback gain Cc (=Cc* in FIG. 2) at this time is detected as a viscosity equivalent value of viscosity.

The equation of motion in the oscillating body 1 is given below, premising that the system of measurement in FIG. 1 is a second order system with a single degree of freedom.

Equation 1

$$m\frac{d^2x}{dt^2} + \left(S\sqrt{\frac{\rho\eta\omega}{2}} - Cc\right)\frac{dx}{dt} + kx = 0 \quad (1)$$

In Equation 1, m denotes an equivalent mass including mass of the oscillating body 1 and additional mass due to motion of the oscillating body 1 and the fluid around the oscillating body 1, S denotes the area (counterface surface) of the oscillating body 1 facing the measured fluid, ρ denotes density of the measured fluid, η denotes viscosity of the measured object, ω denotes the response frequency of the oscillating body 1, Cc denotes velocity feedback gain of the amplifier 5, and k denotes a spring constant of the oscillating body 1.

Note that the facing area S represents the area of a surface of the oscillating body 1 that produces shear force while the oscillating body 1 is moving in the measured fluid. For example, when the oscillating body 1 is a cantilever, the facing area S represents the area of a surface extending parallel to the oscillating direction.

When the response amplitude of the oscillating body 1 is comparatively small, the above-mentioned Equation 1 holds true, and the absolute value of the coefficient of "dx/dt" in Equation 1 is small, the response frequency of the oscillating body 1 takes a value almost equal to the linear natural frequency of the oscillating body 1 independent of the response amplitude according to the linear vibration theory.

When the velocity feedback gain Cc (>0) is increased gradually, and the conditions for the following Equation 2 are thus satisfied, the oscillation system turns into a negative damping system, generating a self-excited oscillation.

Equation 2

$$S\sqrt{\frac{\rho\eta\omega}{2}} - Cc < 0 \quad (2)$$

That is, the velocity feedback gain Cc* (which is referred to as the oscillation limit gain hereafter), which gives the oscillation limit of self-excited oscillation at which the oscillating body 1 may start oscillating, is represented by the following Equation 3.

Equation 3

$$Cc(=Cc^*) = S\sqrt{\frac{\rho\eta\omega}{2}} \quad (3)$$

Therefore, the viscosity η can be calculated using Equation 4 by finding the velocity feedback gain Cc* on the premise that the oscillation limit of the self-excited oscillation is given.

Equation 4

$$\eta = \frac{2}{\rho\omega}\left(\frac{Cc^*}{S}\right)^2 \quad (4)$$

In this manner, the viscosity η can be calculated using the above-mentioned Equation 4. When the response amplitude of the oscillating body 1 is comparatively small, Equation 1 holds true as mentioned above, and the absolute value of the coefficient of the "dx/dt" is small, the response frequency ω will be a constant value almost equal to the linear natural frequency of the oscillating body 1. This fact makes it apparent that the viscosity η corresponds to the velocity feedback gain Cc at the oscillation limit, uniquely.

Therefore, the velocity feedback gain Cc at the time when the oscillating body 1 is oscillating is equal to the velocity feedback gain Cc* when the oscillation limit is given. The velocity feedback gain Cc* at the time when the oscillating body 1 has started oscillating as a result of changing the velocity feedback gain Cc may be used as an equivalent viscosity value representing the degree of viscosity. Furthermore, the viscosity η will be calculated through a calculation using Equation 4.

Note that fluid density ρ and area S of the oscillating body 1, which faces the fluid, are detected beforehand using Equation 4.

Moreover, response frequency ω is obtained by changing the velocity feedback gain Cc, thereby making the oscillating body 1 start self-excited oscillation and then detecting response frequency ω of the oscillating body 1, which is finally used as the response frequency ω. That is, when Equation 1 holds true, as is mentioned above, namely the response amplitude is small and the absolute value of the coefficient of "dx/dt" in Equation 1 is small, the response frequency will be almost equal to the linear natural frequency of the oscillating body 1 according to the linear vibration theory, and will be a constant value irrespective to the response amplitude. Therefore, a highly precise viscosity η can be obtained using as response frequency ω in Equation 4. Namely, the greater the difference between the response frequency used as the response frequency ω of Equation 4 and the natural frequency, the larger the detection error of viscosity η.

Figure 2:
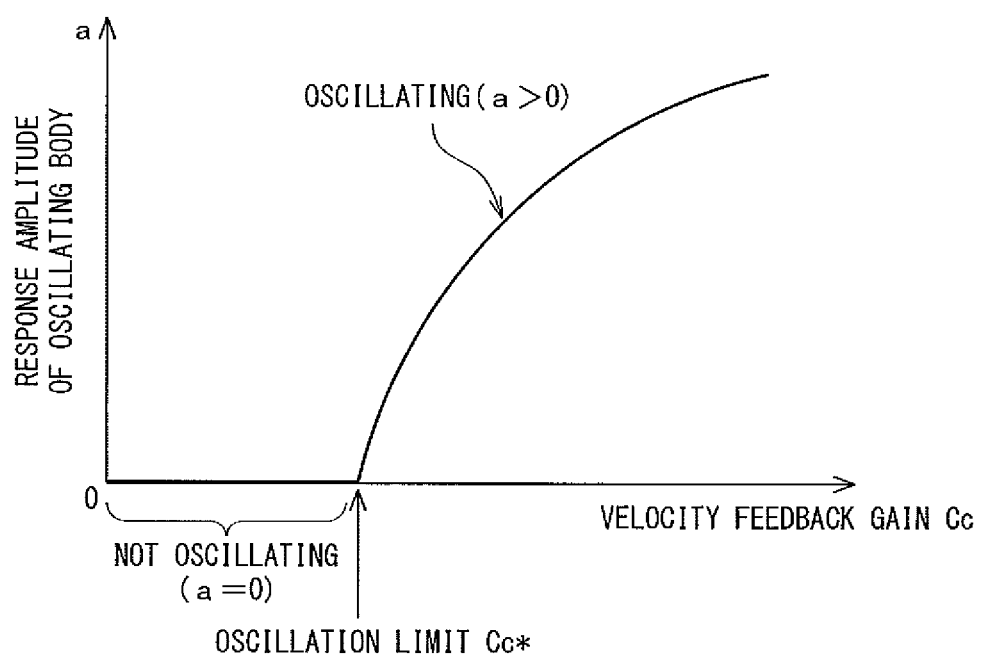
FIG. 2 is a characteristic diagram showing a relationship between velocity feedback gains and corresponding response amplitudes of an oscillating body.

On the other hand, when the oscillating body 1 generates self-excited oscillation, it will oscillate with a single response frequency, where this single response frequency is almost equal to the linear natural frequency when the response amplitude of the oscillating body 1 is small enough. That is, it is a constant value irrespective to the response amplitude, which is apparent theoretically. As shown in FIG. 2, the oscillating body 1 will start self-excited oscillation when the velocity feedback gain Cc reaches the oscillation limit gain Cc*, and when the velocity feedback gain Cc exceeds the oscillation limit gain Cc*, the larger the velocity feedback gain Cc, the larger the response amplitude of the self-excited oscillation. Namely, the closer the value of the velocity feedback gain Cc is to the oscillation limit gain Cc*, the smaller the response amplitude of the self-excited oscillation of the oscillating body 1. Therefore, the response frequency of the oscillating body 1 at the time when the self-excited oscillation starts or when the amplitude becomes smaller is almost equal to the linear natural frequency of the oscillating body 1, and the closer the velocity feedback gain Cc to the oscillation limit gain Cc*, the smaller the difference between the natural frequency and the response frequency of the oscillating body 1 with a constant response frequency irrespective to the amplitude, thereby improving arithmetic accuracy of the Equation 4.

As a result, calculation of the viscosity η using the response frequency of the oscillating body 1 at the time when the self-excited oscillation has started as the response frequency ω in the Equation 4 is equivalent to calculating using the natural frequency of the oscillating body 1, thereby obtaining highly precise viscosity η.

Note that in FIG. 2, the horizontal axis represents the velocity feedback gain Cc, and the vertical axis represents a response amplitude a in the case where a cantilever is applied as the oscillating body 1.

Figure 3:
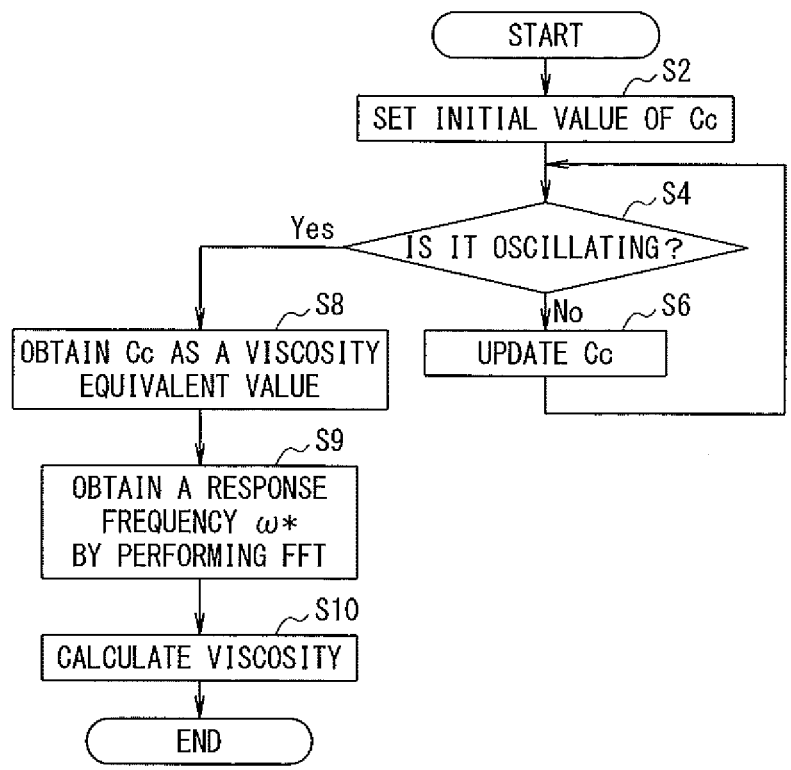
FIG. 3 is a flow chart showing viscosity measurement steps, according to embodiments of the present invention.

To begin with, as is shown in the flowchart of FIG. 3, the velocity feedback gain Cc of the amplifier 5 is set to an initial value (Step S2). This initial value can be set to an arbitrary value, such as zero or a value in the vicinity of the oscillation limit gain Cc* according to a predicted viscosity of the measured fluid.

Next, whether the oscillating body 1 has oscillated is determined either based on the oscillating displacement x of the oscillating body 1 calculated by the displacement detector 3 or the oscillating velocity dx/dt of the oscillating body 1 calculated by the oscillating velocity computing unit 4 (Step S4). As for determination of whether the oscillating body 1 has oscillated, the oscillating body 1 should be determined to have oscillated if the oscillating displacement x or the oscillating velocity dx/dt has changed to a predetermined threshold value or greater. Alternatively, the oscillating body 1 has oscillated is determined, when a spectrum of a single response frequency is generated, by subjecting the oscillating displacement data consisting of oscillating displacements x into FFT (fast Fourier transform) or the like, and thereby finding a frequency spectrum of the response amplitude of the oscillating body 1.

If it is determined in Step S4 that the oscillating body 1 has not oscillated, processing goes to Step S6, in which the velocity feedback gain Cc of the amplifier 5 is then increased, and processing then returns to Step S4. The velocity feedback gain Cc may be changed continuously, or it may otherwise be changed by a predetermined variation.

Until it is determined in Step S4 that the oscillating body 1 has oscillated, the processing in Steps S4 and S6 is repeated, increasing the velocity feedback gain Cc. When the oscillating body 1 starts oscillating, processing goes to Step S8 from Step S4. The velocity feedback gain Cc at this time or the velocity feedback gain Cc at the time when the oscillating body has oscillated is detected as the oscillation limit gain Cc*, which is then viscosity equivalent value of the measured fluid.

Next, it goes to Step S9, in which the velocity feedback gain Cc is maintained at a value of "Cc*+Δc1", which has resulted from adding a predetermined quantity Δc1 to the oscillation limit gain Cc*, for example. The oscillatory waveform data consisting of the oscillating displacements x of the oscillating body 1 is then subjected to spectral analysis through FFT (fast Fourier transform), thereby obtaining a single response frequency in the found spectrum as a response frequency ω* at the oscillation limit.

Note that when the velocity feedback gain Cc is maintained at the value "Cc*+Δc1", "Δc1" is set at a comparatively small value, which allows detection of the response frequency ω* based on the oscillating displacement x of the oscillating body 1. The greater "Δc1", the greater the velocity feedback gain Cc, and the response amplitude of the oscillating body 1 will thus be larger, as shown in FIG. 2. As a result, the response frequency of the oscillating body 1 shifts from its linear natural frequency, causing easy change in the response frequency in response to a slight change in the response amplitude. This means that a detection error of ω in the Equation 4 will be larger, and the viscosity calculation accuracy will thus fall. Therefore, it is preferable that "Δc1" is set to the smallest possible value.

Processing goes to Step S10, in which the oscillation limit gain Cc*, which is the viscosity equivalent value calculated in Step S8, and the response frequency ω* at the oscillation limit calculated in Step S9 are substituted in the above-mentioned Equation 4 so as to calculate the viscosity η.

As such, the viscosity of the fluid is easily detectable merely by changing the velocity feedback gain Cc and detecting the velocity feedback gain Cc (=Cc*) at the time when the oscillating body 1 has started self-excited oscillation, and also detecting the response frequency (=ω*) of the oscillating body 1, which generates self-excited oscillation.

Figure 4A:
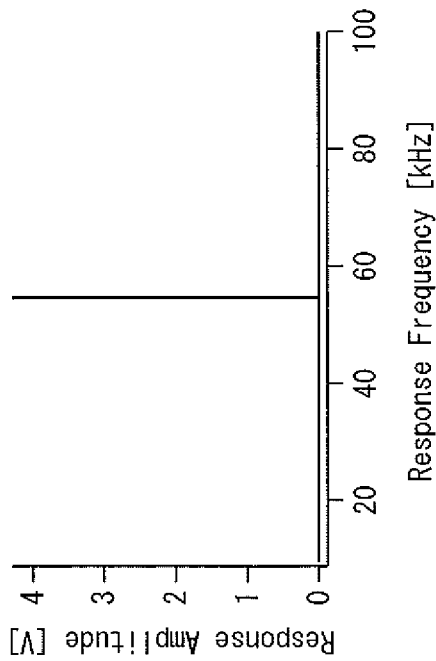
FIG. 4A is a characteristic diagram showing a relationship between the excitation frequency and the corresponding response amplitude of the oscillating body, which is obtained through a viscosity measuring method using external excitation.

According to a conventional viscosity measuring method using an external excitation method for viscosity measurement based on the Q value acquired from a frequency response curve, the Q value is calculated based on the frequency response curve by sweeping excitation frequencies for the oscillating body 1, drawing a frequency response curve for the oscillating body 1, as shown in FIG. 4A, and obtaining the Q value from this frequency response curve. Therefore, it is necessary to change the excitation frequency for the oscillating body 1 little by little, so as to accumulate experimental data and obtain a frequency response curve.

On the other hand, since this embodiment does not need the Q value for viscosity detection, the frequency response curve is unnecessary. Therefore, since a process for creating the frequency response curve is not required, there is an advantage that time and effort for viscosity detection may be substantially reduced.

Figure 4B:
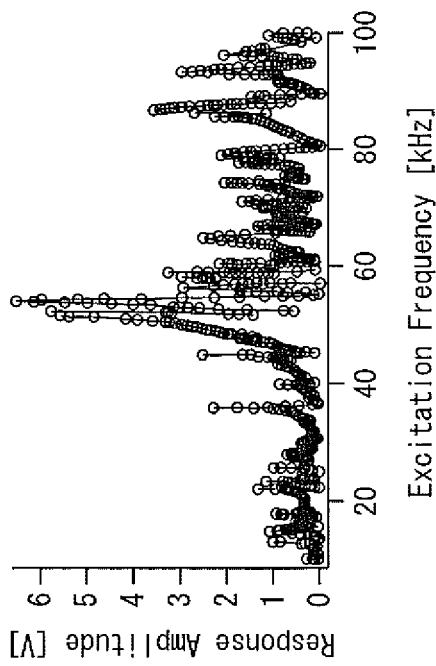
FIG. 4B is a characteristic diagram showing relationship between the response frequency of the oscillating body and the response amplitude of the same obtained through the viscosity measuring method using self-excited oscillation.

In the case of exciting the oscillating body 1, since no peak frequency in the frequency response characteristic curve appears clearly, as shown in FIG. 4A, it is difficult to specify a peak frequency as a viscosity equivalent value with high precision. On the other hand, in the case of making the oscillating body 1 generate self-excited oscillation, as is illustrated in FIG. 4B, the oscillating body 1, even if being in a measured fluid, generates self-excited oscillation with a single frequency. This makes viscosity measurement easy for the following reasons.

In other words, as is illustrated in FIG. 2, even if the velocity feedback gain Cc has been changed, the oscillating body 1 will not oscillate until the velocity feedback gain reaches the oscillation limit, but starts oscillating for the first time when reaching the velocity feedback gain (Cc*), which gives the oscillation limit, resulting in increasing the velocity feedback gain Cc and thereby increasing the response amplitude a.

At this time, the oscillating body 1 oscillates with a single frequency. Therefore, whether oscillation has been generated will be determined easily and accurately merely by detecting a rising edge of the response amplitude a.

Moreover, if the velocity feedback gain Cc, namely the oscillation limit gain Cc* as a viscosity equivalent value, is obtained when the response amplitude a rises, accurate detection of the oscillation limit gain Cc* is possible. As a result, the viscosity η can be detected with high precision.

Note that in FIG. 4A, the horizontal axis represents excitation frequency and the vertical axis represents response amplitude of the oscillating body 1. Moreover, in FIG. 4B, the horizontal axis represents response frequency of the oscillating body 1, and the vertical axis represents response amplitude of the oscillating body 1.

Moreover, use of the above-mentioned viscosity measuring device will provide advantageous results, such as detection of change in viscosity of measured fluid in real time.

That is, as mentioned above, only when the above-mentioned Equation 2 is satisfied, self-excited oscillation will start. Therefore, the viscosity η can be obtained by calculating the above-mentioned Equation 4 using the oscillation limit gain Cc* when the velocity feedback gain Cc has reached the oscillation limit gain Cc*, which gives an oscillation limit.

Afterwards, a predetermined quantity Δc2 is added to the oscillation limit gain Cc* at which self-excited oscillation starts, and the velocity feedback gain Cc is maintained at the added value "Cc*+Δc2." As a result, the oscillating body 1 will perform self-excited oscillation with a constant amplitude.

When the viscosity of the measured fluid changes to be greater, Equation 2 cannot be satisfied, and the self-excited oscillation thus stops. In this case, the velocity feedback gain Cc increases. This allows finding of an updated oscillation limit gain Cc* by monitoring whether amplitude develops.

Therefore, with the velocity feedback gain Cc being maintained at "Cc*+Δc2", real time detection of whether viscosity has increased is possible by monitoring whether the oscillating body 1 has changed from the self-excited oscillating mode with a constant amplitude to a non-oscillation mode.

Moreover, by finding the relationship between viscosity of each measured fluid and corresponding velocity feedback gain Cc ahead of time, it is possible to quantitatively determine how much the viscosity has changed, based on relationship between the oscillation limit gains Cc* before and after the change in the viscosity of measured fluid.

On the other hand, in the case where the viscosity of the measured fluid has changed, with the velocity feedback gain Cc being maintained at "Cc*+Δc2", which has resulted from adding a predetermined quantity Δc2 to the oscillation limit gain Cc*, and where the viscosity has become smaller, the amplitude of the oscillating body 1 that has been self-excitedly oscillating with a constant amplitude will be larger. At this time, making the velocity feedback gain Cc decrease will make the amplitude of self-excited vibration smaller and will also make the velocity feedback gain Cc at the time when no self excitation amplitude appears be the oscillation limit gain Cc* for the measured fluid after the viscosity has changed.

Therefore, with the velocity feedback gain Cc being maintained at the value "Cc*+Δc2", monitoring whether the amplitude of the oscillating body 1, which has been self-excitedly oscillating with a constant amplitude, has become larger will allow real time detection of whether the viscosity of the measured fluid has decreased, and will allow quantitative measurement of increase in the viscosity in the same manner as described above.

Note that with the velocity feedback gain Cc being maintained at "Cc*+Δc2", the predetermined quantity Δc2 should be such a value that will allow detection of the fact that the oscillating body 1 has changed from the oscillating mode to the non-oscillation mode, based on the response amplitude of the oscillating body 1, and will also allow accurate detection of change in the amplitude of the oscillating body 1. In the case where "Δc2" is large, even when the viscosity is large, the self-excited oscillation continues until Equation 2 is not satisfied. Sensitivity to change in the viscosity becomes low accordingly. Therefore, the value of "Δc2" may be set in light of the sensitivity to change in the viscosity.

The viscosity η is calculated by detecting the oscillation limit gain Cc* and the response frequency ω* at the oscillation limit and using Equation 4. The response frequency ω* is a response frequency of the oscillating body 1, with the velocity feedback gain Cc being maintained at the value "Cc*+Δc1", which has resulted from adding the predetermined quantity Δd1 to the oscillation limit gain Cc*, as mentioned above, and the predetermined quantity "Δc1" is set at a certain value so that the response amplitude is a comparatively small value that allows detection of the response frequency. Therefore, the difference between the detected response frequency ω* and the natural frequency of the oscillating body 1 may be small. That is, the natural frequency of the oscillating body 1 is detectable with high precision.

Therefore, the detection precision of the viscosity η may be improved by using the natural frequency (=the response frequency ω*) of the oscillating body 1 detected with high precision and the oscillation limit gain Cc* also detected with high precision to calculate the viscosity η.

In addition, viscosity measurement may be performed easily with high precision in real time. It is important for food manufacturers, for example, to perform viscosity measurement of developed product precisely for chemical indices for quality of food, taste, and chewing sensation. Also for chemical measuring instrument manufacturers, it is important to improve the measurement accuracy of viscosity for improvement in usability.

Therefore, easy viscosity measurement with high precision is possible by applying the viscosity measuring method to the fields in which viscosity measurement is important, such as foods or chemical measuring instruments. As a result, improvement in working efficiency will be attained suitably.

The case where the first embodiment described above obtains the velocity feedback gain Cc as a viscosity equivalent value, and the viscosity η is calculated based thereon is explained. However, the present invention is not limited to this measure. For example, in the case where only detection of change in viscosity is required, the detected velocity feedback gain Cc may be used as a viscosity equivalent value representing the viscosity so as to detect change in the viscosity equivalent value and determine whether the viscosity has changed.

Moreover, while in the first embodiment described above, the case where the response frequency ω* at the oscillation limit is used as the response frequency ω in Equation 4 is explained. However, the present invention is not limited to this case.

As mentioned above, the response frequency ω is almost equal to the natural frequency when the system of measurement is a second order system with a single degree of freedom, and the response amplitude of the oscillating body 1 is comparatively small. Therefore, in the case where the system of measurement is a second order system with a single degree of freedom, and the response amplitude of the oscillating body 1 is comparatively small, and very high precision is not required for measurement of the viscosity η, $(k/m)^{1/2}$ equivalent of the natural frequency may be used as the response frequency ω. Note that k denotes a spring constant of the oscillating body 1, and m denotes an equivalent mass including mass of the oscillating body 1 and additional mass due to motions of the oscillating body 1 and the fluid around the oscillating body 1.

The case where the velocity feedback gain Cc is output as a viscosity equivalent value from the viscosity measuring device, according to the first embodiment, has been explained. However, the present invention is not limited to this case.

Figure 5:
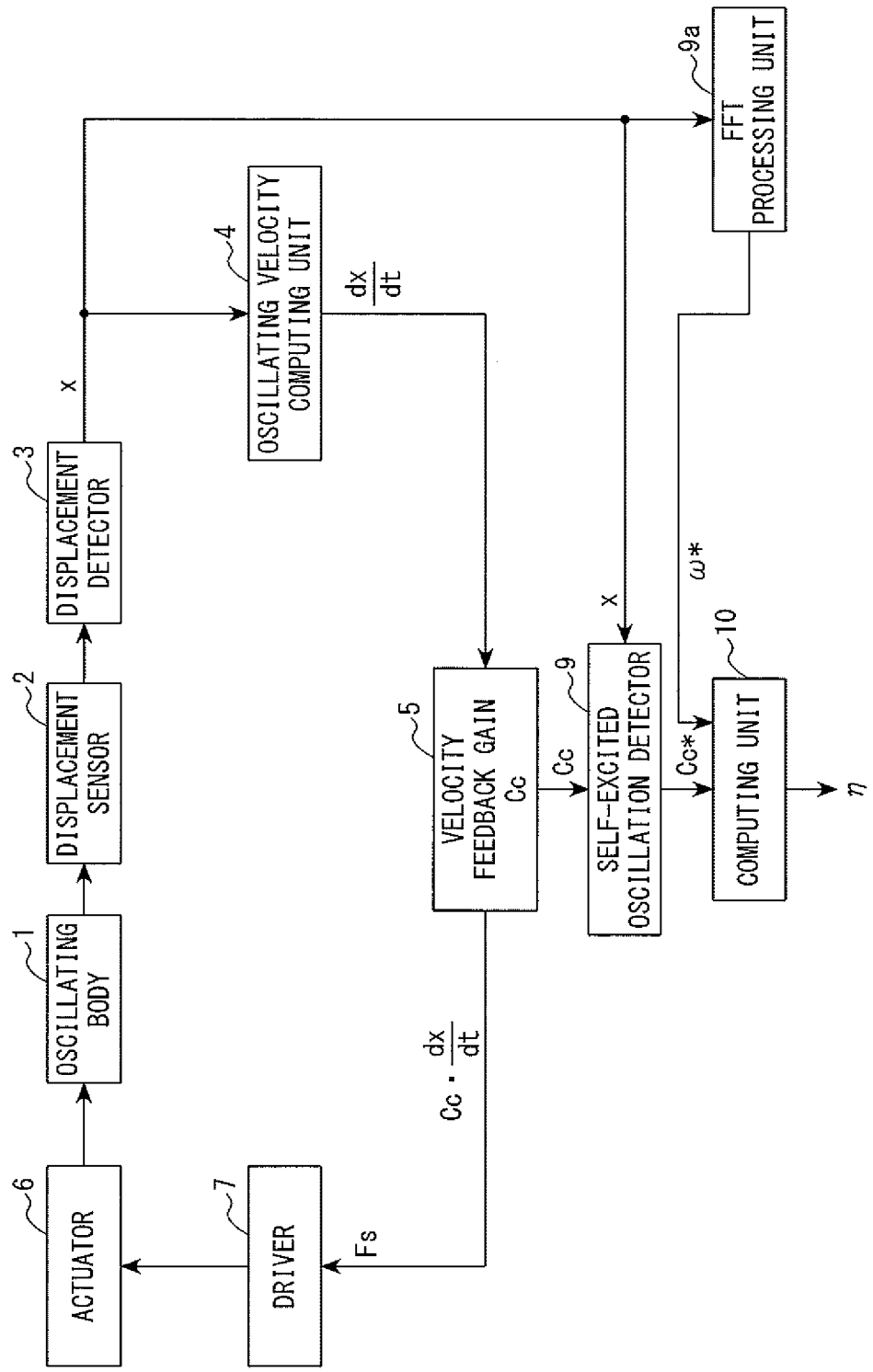
FIG. 5 is a schematic block diagram showing another working example of the first embodiment.

For example, as illustrated in FIG. 5, a self-excited oscillation detector 9 for detection of whether the oscillating body 1 is self-excitedly oscillating, based on an oscillating displacement x (or an oscillating velocity dx/dt or a frequency spectrum of response amplitude); an FFT processing unit 9a for carrying out a fast Fourier transform of oscillatory waveform data made up of oscillating displacements x and calculation of response frequency; and a computing unit 10 are provided. With this configuration, the velocity feedback gain Cc is changed, and the self-excited oscillation detector 9 detects the velocity feedback gain Cc of the amplifier 5 while the oscillating body 1 is self-excitedly oscillating. Then, with the velocity feedback gain Cc being maintained at a value of "Cc*+Δc1", which has resulted from adding a predetermined quantity Δc1 to the oscillation limit gain Cc* when self-excited oscillation occurs, the FFT processing unit 9a carries out a fast Fourier transform of the oscillatory waveform data made up of oscillating displacements x of the oscillating body 1, and calculates a response frequency.

Figure 6:
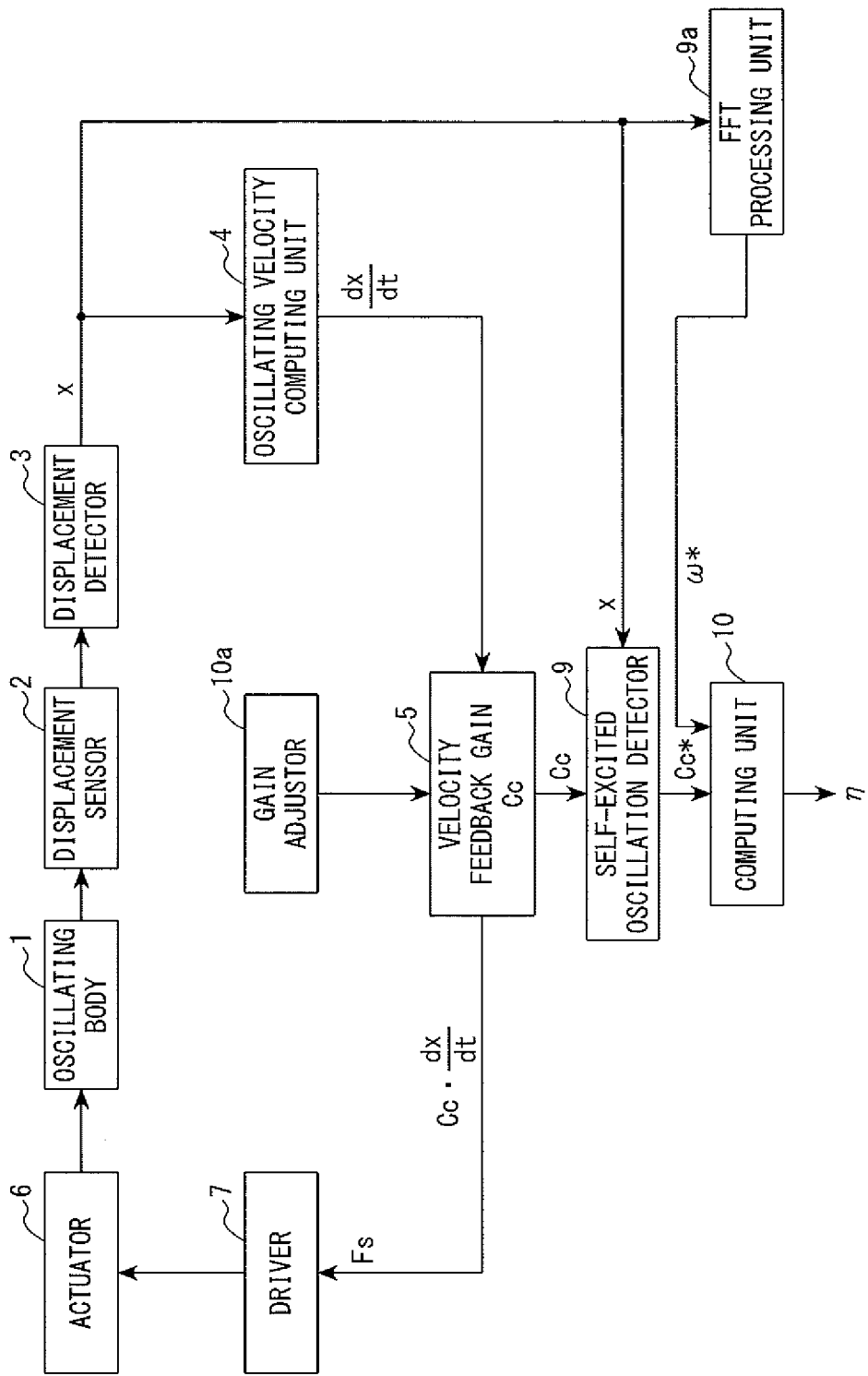
FIG. 6 is a schematic block diagram showing another working example of the first embodiment.

The computing unit 10 may calculate the viscosity η based on Equation 4 by letting the response frequency detected by the FFT processing unit 9a be a response frequency ω* at the oscillation limit, and using the response frequency w* and the oscillation limit gain Cc* detected by the self-excited oscillation detector 9. Furthermore, as illustrated in FIG. 6, a gain adjustor 10a for changing the velocity feedback gain Cc automatically may be provided, automatically adjusting the velocity feedback gain Cc.

Moreover, in such a configuration that the first embodiment has a processing unit, such as a microcomputer, an A/D converter, and a D/A converter, and the processing unit receives an output from a displacement sensor 2 via the A/D converter, operations of the displacement detector 3 and the oscillating velocity computing unit 4 and the velocity feedback gain Cc are changed. The processing unit multiplies the oscillating velocity dx/dt by the output from the displacement sensor 2 digitally so that a feedback control signal Fs is generated; and feedback control signal Fs is output to the driver 7 via the D/A converter.

In this case, such a configuration is possible whereby: the processing unit monitors whether the oscillating body 1 has oscillated, based on the oscillating displacements x detected by the displacement detector 3 or the oscillating velocity dx/dt calculated by the oscillating velocity computing unit 4; and the velocity feedback gain Cc when the oscillating body 1 has oscillated is set as the oscillation limit gain Cc*, which is then received as a viscosity equivalent value; and the oscillation limit gain Cc* is then output as the result of viscosity measurement to an output unit, such as a display, thereby notifying an operator.

Furthermore, such a configuration is possible whereby: the processing unit executes processing for maintaining the velocity feedback gain Cc at "Cc*+Δc1" and generating a self-excited oscillation after the oscillation limit gain Cc* is detected; FFT processing for the response frequency of the self-excited oscillation and calculating the response frequency ω* at the oscillation limit; and calculating the viscosity η using the oscillation limit gain Cc* and the response frequency ω* according to Equation 4. Namely, such a configuration that the processing unit executes respective processing of the displacement detector 3, the oscillating velocity computing unit 4, the amplifier 5, the self-excited oscillation detector 9, the FFT processing unit 9a, the computing unit 10, and the gain adjustor 10a in FIG. 6, so as to automatically calculate the viscosity η and notify an operator, is possible.

Next, the second embodiment of the present invention will be described. This second embodiment aims to further reduce the amplitude developed while the oscillating body 1 is self-excitedly oscillating below that attained in the first embodiment.

Figure 7:
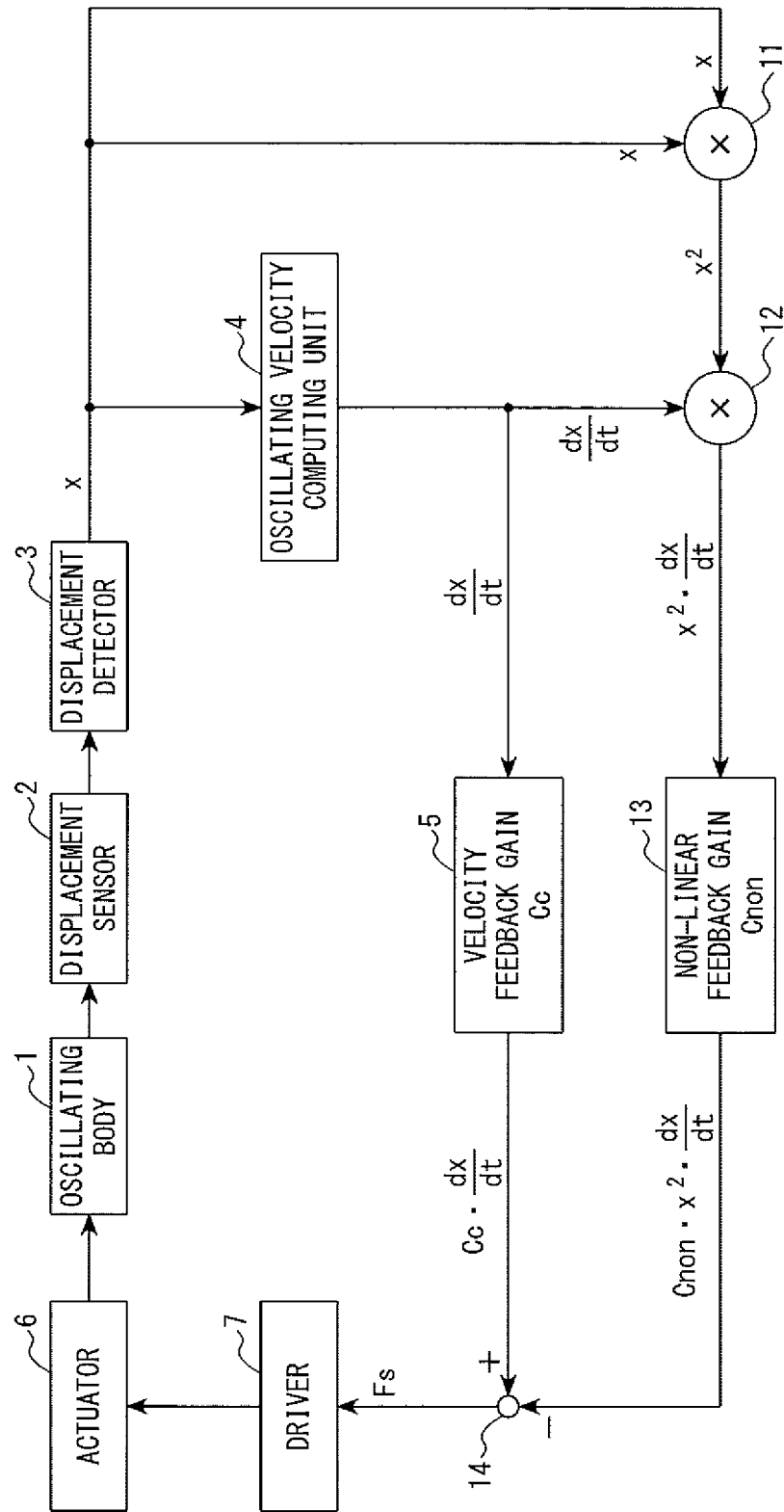
FIG. 7 is a schematic block diagram showing a working example of a viscosity measuring device according to a second embodiment.

FIG. 7 is a schematic block diagram showing an outline structure of a viscosity measuring device according to the second embodiment. The same reference numerals are given to the same corresponding units as those of the viscosity measuring device according to the first embodiment shown in FIG. 1, and detailed description thereof is omitted.

As illustrated in FIG. 7, the viscosity measuring device of the second embodiment includes the oscillating body 1, such as a cantilever, the displacement sensor 2 for measuring the oscillating displacement of the oscillating body 1, the displacement detector 3, the oscillating velocity computing unit 4, the amplifier 5, the actuator 6 for oscillating the oscillating body 1, and the driver 7 for driving the actuator 6. In addition, it also includes multipliers 11 and 12, an amplifier 13, and a computing unit 14.

The multiplier 11 receives the oscillating displacement x from the displacement detector 3, squares the received oscillating displacement x, so as to find $x^2$, and transmits it to the multiplier 12.

The multiplier 12 receives the oscillating velocity dx/dt from the oscillating velocity computing unit 4, multiplies this oscillating velocity dx/dt by the product $x^2$ calculated by the multiplier 11, and transmits the product "$x^2 \cdot (dx/dt)$" to the amplifier 13.

The amplifier 13 multiplies the product "$x^2 \cdot (dx/dt)$" calculated by the multiplier 12 by a positive nonlinear feedback gain Cnon, resulting in product "$Cnon \cdot x^2 \cdot (dx/dt)$", and the product "$Cnon \cdot x^2 \cdot (dx/dt)$" is then transmitted to the computing unit 14.

The computing unit 14 subtracts the value "$Cnon \cdot x^2 \cdot (dx/dt)$" that is output from the amplifier 13 from the value "$Cc \cdot (dx/dt)$" that is output from the amplifier 5, and transmits the subtracted result "$Cc \cdot (dx/dt) - Cnon \cdot x^2 \cdot (dx/dt)$" to the driver 7 as a feedback control signal Fs.

Next, a viscosity measuring method according to the second embodiment will be explained.

The driver 7 is activated, driving the actuator 6, and the actuator 6 thus applies force or moment of force, torque, to the oscillating body 1. Displacement of the oscillating body 1 is detected by the displacement sensor 2, and the oscillating displacement x of the oscillating body 1 is detected by the displacement detector 3, based on the output from the displacement sensor 2. This oscillating displacement x is transmitted to the oscillating velocity computing unit 4, which then calculates the oscillating velocity dx/dt. The amplifier 5 multiplies this oscillating velocity dx/dt by the velocity feedback gain Cc, which is a linear feedback gain.

Moreover, the multiplier 11 calculates $x^2$ based on the oscillating displacement detected by the displacement detector 3, and the multiplier 12 multiplies $x^2$ by the oscillating velocity dx/dt calculated by the oscillating velocity computing unit 4, and the amplifier 13 multiplies the nonlinear feedback gain Cnon by the product "$x^2 \cdot (dx/dt)$" calculated by the multiplier 12. The computing unit 14 subtracts the value "$Cnon \cdot x^2 \cdot (dx/dt)$" output by the amplifier 13 from the value "Cc·dx/dt" output by the amplifier 5, and the subtracted result "Cc·(dx/dt)−Cnon·x²·(dx/dt)" is transmitted to the driver 7 as the feedback control signal Fs. The driver 7 amplifies the feedback control signal Fs, thereby driving the actuator 6. As a result, force or moment of force, torque, is applied to the oscillating body 1.

The feedback control signal Fs is expressed by the following Equation 5:

$$Fs = Cc \cdot (dx/dt) - Cnon \cdot x^2 \cdot (dx/dt) \quad (5)$$

where "Cc·(dx/dt)" denotes a term of a linear component for the oscillating velocity dx/dt of the oscillating body 1, and "Cnon·x²·(dx/dt)" denotes a term of a nonlinear component for the oscillating displacement x and the oscillating velocity dx/dt of the oscillating body 1. When a cantilever is used as the oscillating body 1, and the nonlinear component balances with the self-excited oscillating force of the cantilever, which is the oscillating body 1, the response amplitude of the cantilever is maintained constantly according to the characteristics of this feedback control. At this time, making the nonlinear feedback gain greater will control the response amplitude of the oscillating body 1 to be smaller so that the response frequency of the oscillating body 1 can be maintained at a fixed linear natural frequency irrespective to the response amplitude.

As a result, the Reynolds number of the system of measurement is lowered, thereby maintaining laminar flow, preventing development of an eddy due to oscillation of the oscillating body 1, and adding up to improvement in accuracy of viscosity measurement. Therefore, amplitude reduction control for reducing the response amplitude at the time of self-excited oscillation should be carried out. Namely, a nonlinear feedback component should be prepared, as is illustrated in FIG. 7. In other words, making the oscillating body 1 oscillate in nonlinear feedback will reduce the amplitude of self-excited oscillation of the oscillating body 1, leading to prevention of development of an eddy, keeping laminar flow, and thereby preventing development of turbulent flow. As mentioned above, the more the response amplitude is reduced, the smaller the difference between the response frequency $\omega^*$ at the oscillation limit and the natural frequency of the oscillating body 1, and the response frequency $\omega^*$ may thus almost match the linear natural frequency. This allows detection of the oscillation limit gain $Cc^*$ and the response frequency $\omega^*$ at the oscillation limit as the natural frequency with higher accuracy. Therefore, the detection precision of viscosity η calculated using the oscillation limit gain $Cc^*$ and the response frequency $\omega^*$ at the oscillation limit may be further improved.

Note that the nonlinear feedback gain Cnon should be set up in the following manner. Namely, since a greater nonlinear feedback gain Cnon allows a lower response amplitude, a certain value, which allows correct detection of oscillation of the oscillating body 1 based on its amplitude where the oscillation is induced at the time when the nonlinear feedback gain Cnon is a comparatively large value and the linear feedback gain Cc has reached the oscillation limit gain $Cc^*$, should be detected beforehand and set as the nonlinear feedback gain Cnon.

In such a manner, generation of an eddy in measured fluid due to self-excited oscillation of the cantilever may be suppressed, thereby preventing development of turbulent flow and making the difference between the response frequency $\omega^*$ at the oscillation limit and the linear natural frequency smaller. As a result, the response frequency will not change according to change in the response amplitude, and the accuracy of viscosity measurement may thus be improved.

Note that the second embodiment may detect change in the viscosity of the fluid by using the velocity feedback gain $Cc^*$ at the time when self-excited oscillation has occurred as a viscosity equivalent value representing viscosity, and by monitoring the viscosity equivalent value.

Figure 8:
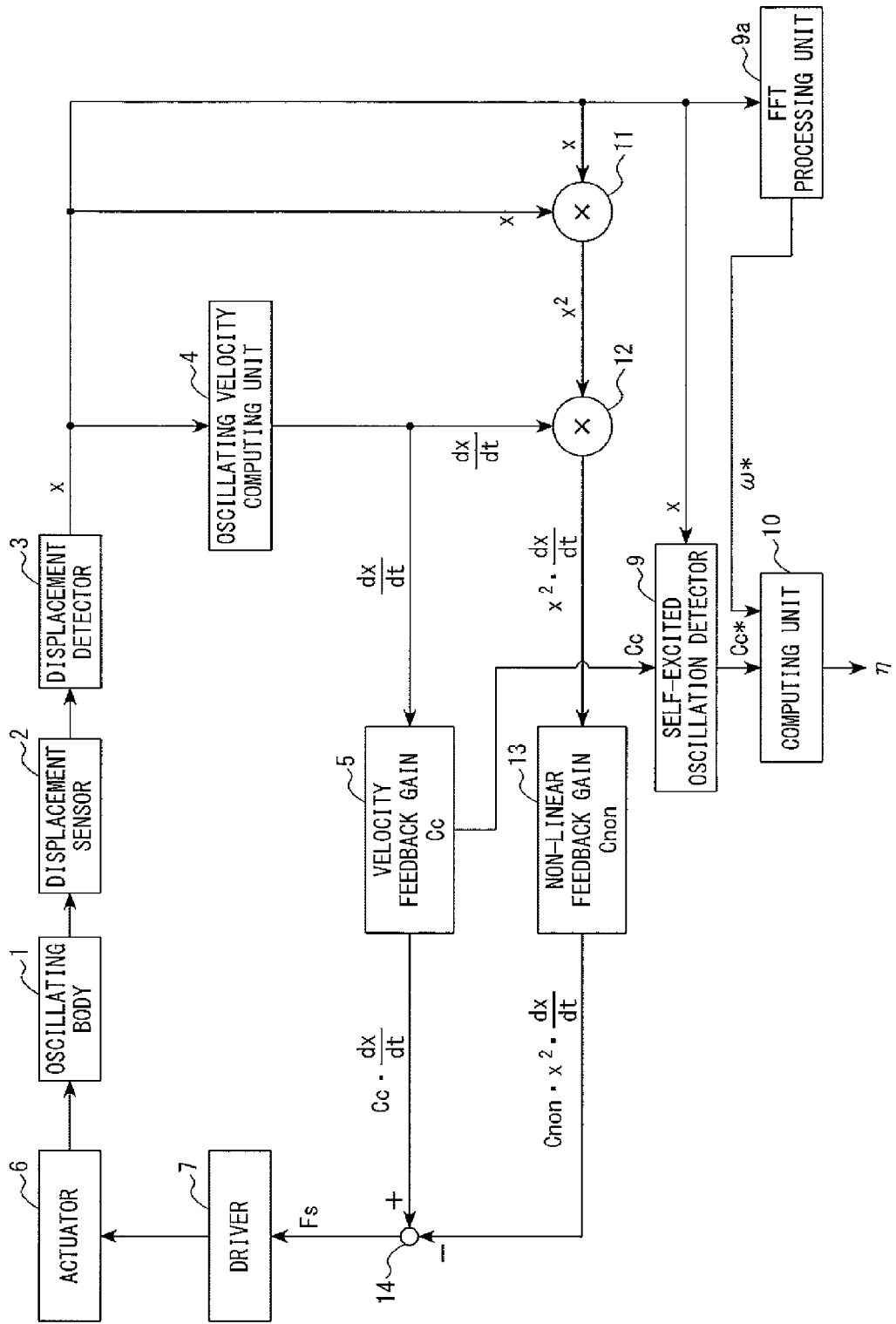
FIG. 8 is a schematic block diagram showing another working example of the second embodiment.

Moreover, as is illustrated in FIG. 8, the self-excited oscillation detector 9 for detection of whether the oscillating body 1 is self-excitedly oscillating, based on the oscillating displacement x (or oscillating velocity dx/dt or frequency spectrum of response amplitude), the FFT processing unit 9a for carrying out a fast Fourier transform of the oscillatory waveform data made up of oscillating displacements x, and for calculating response frequency, and the computing unit 10 are provided as in the first embodiment. After the self-excited oscillation detector 9 has detected the velocity feedback gain Cc of the amplifier 5 developed while the oscillating body 1 undergoes self-excited oscillation, the velocity feedback gain Cc is increased so as to be "$Cc^*+\Delta c1$", which has resulted from adding the predetermined quantity "$\Delta c1$" to the oscillation limit gain $Cc^*$ developed when self-excited oscillation occurs, and at this time, a fast Fourier transform of the oscillatory waveform data made up of oscillating displacements x of the oscillating body 1 is performed by the FFT processing unit 9a, and the response frequency is then obtained. Afterwards, the response frequency found by the FFT processing unit 9a is used as the response frequency $\omega^*$ at the oscillation limit. The computing unit 10 calculates the viscosity η using the response frequency $\omega^*$ and the oscillation limit gain $Cc^*$ obtained by the self-excited oscillation detector 9 according to Equation 4.

Furthermore, a processing unit, such as a microcomputer, an A/D converter, and a D/A converter may be provided. An output from the displacement sensor 2 is received by the processing unit via the A/D converter, and the processing unit then digitally executes processing for the displacement detector 3 and the oscillating velocity computing unit 4, changing the velocity feedback gain Cc, and calculations for the amplifiers 5 and 13 and the computing unit 14, thereby generating the feedback control signal Fs and then outputting it to the driver 7 via the D/A converter. Moreover, the processing unit may also execute: processing for obtaining the oscillation limit gain $Cc^*$, which is a velocity feedback gain when self-excited oscillation has been detected; FFT processing of the oscillatory waveform data made up of oscillating displacements x of the oscillating body 1 at this time, with the velocity feedback gain Cc being maintained at "$Cc^*+\Delta c1$"; calculation of the response frequency; setting the calculated response frequency as the response frequency $\omega^*$ at the oscillation limit; and calculation of the viscosity η based on the oscillation limit gain $Cc^*$ and the response frequency $\omega^*$.

Alternatively, in each above-mentioned embodiment, the oscillating displacements x of the oscillating body 1 detected by the displacement detector 3 may be output to a monitoring device, etc., and an operator can thus monitor the oscillation of the oscillating body 1 with the monitoring device.

Moreover, in each above-mentioned embodiment, the case where the cantilever is applied as the oscillating body 1 is explained. However, the present invention is not limited to this case. For example, the conventional oscillating viscometer, such as a viscometer using a rotary cylinder, parallel plates, or the like may be applied.

Moreover, the case where the velocity feedback gain Cc is increased from a comparatively small value is explained in each above-mentioned embodiment. However, the present invention is not limited to this case, and the velocity feedback gain Cc may be decreased from a comparatively large value.

In this case, since the velocity feed gain Cc is large, the oscillating body 1 will start self-excited oscillation as the actuator 6 is activated. Therefore, the time when the self-excited oscillation of the oscillating body 1 stops should be detected, and the velocity feedback gain Cc at this time should be detected as the oscillation limit gain Cc*.

Moreover, the velocity feedback gain Cc may be changed continuously in each above-mentioned embodiment. Furthermore, it may be changed gradually, such as by Δc. When changing the velocity feedback gain Cc gradually, change in the velocity feedback gain Cc (e.g., Δc) is a detection error for the oscillation limit gain. Therefore, change in the velocity feedback gain should be set according to a target viscosity precision.

Moreover, in each above-mentioned embodiment, the case where the velocity feedback gain Cc at the time when self-excited oscillation has occurred is detected in real time as the viscosity equivalent value is explained. However, the present invention is not limited to this case.

For example, a memory is provided, the oscillating displacement x of the oscillating body 1 or the oscillating velocity dx/dt is detected while changing the velocity feedback gain Cc within a predetermined range, and the detected value is then associated with the velocity feedback gain Cc and stored as correspondence information in the memory. Once the correspondence information is obtained, the correspondence information stored in the memory is read out, and, based on this, the velocity feedback gain Cc when the oscillation limit is reached may be obtained as the viscosity equivalent value.

Note that in the embodiment described above, the displacement detector 3 corresponds to the oscillating displacement detector, the oscillating velocity computing unit 4 corresponds to the oscillating velocity detector, and the self-excited oscillation detector 9 and the computing unit 10 correspond to the viscosity equivalent value detector.

Moreover, in the first embodiment, the amplifier 5 corresponds to the controller, and in the second embodiment, the amplifier 5, the multipliers 11 and 12, the amplifier 13, and the computing unit 14 correspond to the controller, and the feedback system made up of the multipliers 11 and 12, the amplifier 13, and the computing unit 14 corresponds to the response amplitude reducer.

The invention claimed is:

1. A viscosity measuring method, using a viscosity measuring device comprising:
an oscillating body put in a fluid to be measured;
an actuator for making the oscillating body oscillate self-excitedly;
an oscillating velocity detector for detecting an oscillating velocity of the oscillating body; and
a controller that generates positive feedback of the oscillating velocity detected by the oscillating velocity detector so as to activate the actuator according to a feedback control signal Fs represented by an equation:

$$Fs=Cc \cdot (dx/dt),$$

where Fs denotes a feedback control signal, Cc denotes a linear velocity feedback gain, and dx/dt denotes the oscillating velocity of the oscillating body;
wherein the viscosity measuring method comprises the steps of:
changing the linear velocity feedback gain for feedback control;
using the linear velocity feedback gain at a time when the oscillating body changes between a non-oscillation mode and an oscillating mode as an oscillation limit gain; and
detecting the oscillation limit gain as a viscosity equivalent value representing viscosity of the fluid.

2. The viscosity measuring method of claim 1, wherein:
the viscosity measuring device further comprises an oscillating displacement detector for detection of oscillating displacement of the oscillating body, and
the controller comprises a response amplitude reducer for reduction of a response amplitude of the oscillating body based on the oscillating velocity and the oscillating displacement detected by the oscillating displacement detector, and the feedback control using the actuator is carried out according to the feedback control signal Fs further represented by an equation:

$$Fs=(Cc-Cnon \cdot x^2) \cdot (dx/dt),$$

Where Cnon denotes a nonlinear feedback gain, and x denotes the oscillating displacement of the oscillating body.

3. The viscosity measuring method of claim 1, further comprising a step of:
calculating the viscosity η of the fluid using an equation:

$$\eta=\{2/(\rho \cdot \omega)\} \times (Cc/S)^2,$$

where ρ denotes a density of the fluid to be measured, ω denotes a response frequency of the oscillating body, and S denotes a surface area of the oscillating body facing the fluid,
wherein the oscillation limit gain is used as the linear velocity feedback gain Cc in the equation, and the response frequency ω in the equation is set to the response frequency of the oscillating body when the linear velocity feedback gain is equal to the oscillation limit gain.

4. The viscosity measuring method of Claim 1, wherein the oscillating body is a cantilever.

5. A viscosity measuring device, comprising:
an oscillating body put in a fluid to be measured;
an actuator for making the oscillating body oscillate self-excitedly;
an oscillating velocity detector for detection of an oscillating velocity of the oscillating body;
a controller that generates positive feedback of the oscillating velocity detected by the oscillating velocity detector so as to feedback control the actuator according to a feedback control signal Fs represented by an equation:

$$Fs=Cc \cdot (dx/dt),$$

where Fs denotes a feedback control signal, Cc denotes a linear velocity feeedback gain, and dx/dt denotes the oscillating velocity of the oscillating body;
a gain adjustor for changing the linear velocity feedback gain of the controller; and
a viscosity equivalent value detector for setting the linear velocity feedback gain at a time when the oscillating body changes between a non-oscillation mode and an oscillating mode as an oscillation limit gain for giving an oscillation limit, and for detecting the oscillation limit gain as a viscosity equivalent value representing viscosity of the fluid.

6. The viscosity measuring device of claim 5, wherein the oscillating body is a cantilever.

7. The viscosity measuring method of claim 2, wherein the oscillating body is a cantilever.

8. The viscosity measuring method of claim 2, further comprising a step of:

calculating the viscosity η of the fluid using an equation:

$$\eta = \{2/(\rho \cdot \omega)\} \times (Cc/S)^2,$$

where ρ denotes a density of the fluid to be measured, ω denotes a response frequency of the oscillating body, and S denotes a surface area of the oscillating body facing the fluid,
    wherein the oscillation limit gain is used as the linear velocity feedback gain Cc in the equation, and the response frequency ω in the equation is set to the response frequency of the oscillating body when the linear velocity feedback gain is equal to the oscillation limit gain.

9. The viscosity measuring method of claim 8, wherein the oscillating body is a cantilever.

\* \* \* \* \*